United States Patent [19]

Holtkamp

[11] Plant 4,348

[45] Dec. 19, 1978

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,052

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Beall & Jeffery

[57] ABSTRACT

An African violet known by the cultivar name Louisiana having light pink, single, non-dropping flowers with frilled edges, the flowers being carried on upright and relatively short stems. The flowers appear just above the rosette of dark green leaves. The cultivar also has a compact habit and excellent growth characteristics.

1 Drawing Figure

1

The present invention comprises a new and distinct cultivar of African violet plant, botanically known as *Saintpaulia ionantha,* and hereinafter referred to by the cultivar name Louisiana. The new cultivar was identified during the breeding and selection process by the number 16/15 - 84/77. Louisiana is a product of a planned breeding program which had the objective of creating a new African violet cultivar having slightly frilled, non-dropping flowers light pink in flower color and carried on relatively short flower stems. These traits in combination were not present in previously available commercial cultivars.

The new cultivar was originated from a cross made in a controlled breeding program in Isselburg, Rhineland, Germany. The female, or seed parent is identified by the designation F III pink frilled (color RHS 62 D). The male, or pollen parent, is identified as XIX 4395 pink star (color RHS 65 A).

Louisiana was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Louisiana, which in combination distinguish this African violet as a new and distinct cultivar:

1. Upright and relatively short, strong flower stems.
2. The flowers are light pink in color, with frilled edges and appear just above the rosette of leaves.
3. 4–6 single flowers on each flower stem, with the first flowering; a plant fully in bloom has 7–9 flower stems.
4. The flowers do not drop.
5. Compact habit and excellent growth characteristic.
6. Dark green leaves.

The accompanying photographic drawing shows a typical specimen plant of the new cultivar, with the

2 photograph showing a plant 8 weeks after potting. The colors appearing in the photograph are as true as possible with color illustrations of this type.

In the description, color references are made to the Royal Horticultural Society color chart (RHS), 1966 edition, except where general color terms of ordinary significance are obvious.

Botanical classification: *Saintpaulia ionantha,* Ramat. cv Louisiana.

Parentage:

*Male parent.*—F III pink frilled (RHS 62 D).

*Female parent.*—XIX 4395 pink star (RHS 65 A).

Propagation: The new cultivar holds its distinguishing characteristics through successive propagations by leaf cuttings and by division of shoots.

Plant: From 6 cm. to 8 cm. tall when grown in pots, and approximately 20 cm. in diameter when fully grown.

*Leaves.*—General form: Oblong. Diameter: 40–55 mm. Texture: Tender, slightly hairy. Aspect: Medium-dark green leaves, borders slightly serrated. Veins: Well pronounced. Color (upperside): 147 A. Color (underside): Young leaves 70 C; old leaves 70 B. Petiole: Brownish red.

*Flowers.*—Buds: Round, diameter 6–7 mm. Sepals: five, 4–5 mm. long. Color: 199 A. Calyx: funnel-shaped. Aspect: flowers and seed vessel connected. Peduncle: upright, erect.

*Individual flowers.*—Size: 45 mm. in total flower diameter. Color: Upperside: 56 B to 56 C, generally apple blossom in color. Underside: 56 C. Borne: Most flower stems carry up to 6 flowers. Shape: Five petals, two small and three large; the three large petals are 20–22 mm. long and 18–19 mm. wide; the two small petals are 15-16 mm. long and 14–15 mm. wide. Arrangement: Carried on upright and erect flower stems, diameter 2 mm.; up to six flowers on each stem. Flowering time: 7–9 weeks after potting, the first flowers will show; after 10–11 weeks, the plant is fully in bloom.

*Reproductive organs.*—Stamens: two stamens, color 7 A. Anthers: four anthers, close together. Arrangement: Underneath the seed vessel, the stamens are connected to the receptacle by two short stems. Styles 6–7 mm. long, color 186 C. Pollen color: 158 B.

*Roots.*—Well developed; young roots are white, turning brownish in color with age.

*Disease resistance.*—No disease problems noted to date.

*General observations.*—Louisiana is a very compact plant with excellent growth characteristics. When blooming for the first time, it has 7–9 upright stems, with up to 6 single flowers and buds on each stem. The pink color of the flower is very similar to that of an apple blossom, and the edges of the flower are frilled. The dark green foliage color provides a pleasant contrast with the flower color.

I claim:

1. A new and distinct cultivar of African violet known by the cultivar name Louisiana and characterized by the combined features of light pink, single, non-dropping flowers having frilled edges and carried on upright and relatively short stems, with the flowers appearing just above the rosette of dark green leaves; and by its compact habit and excellent growth characteristics.

* * * * *

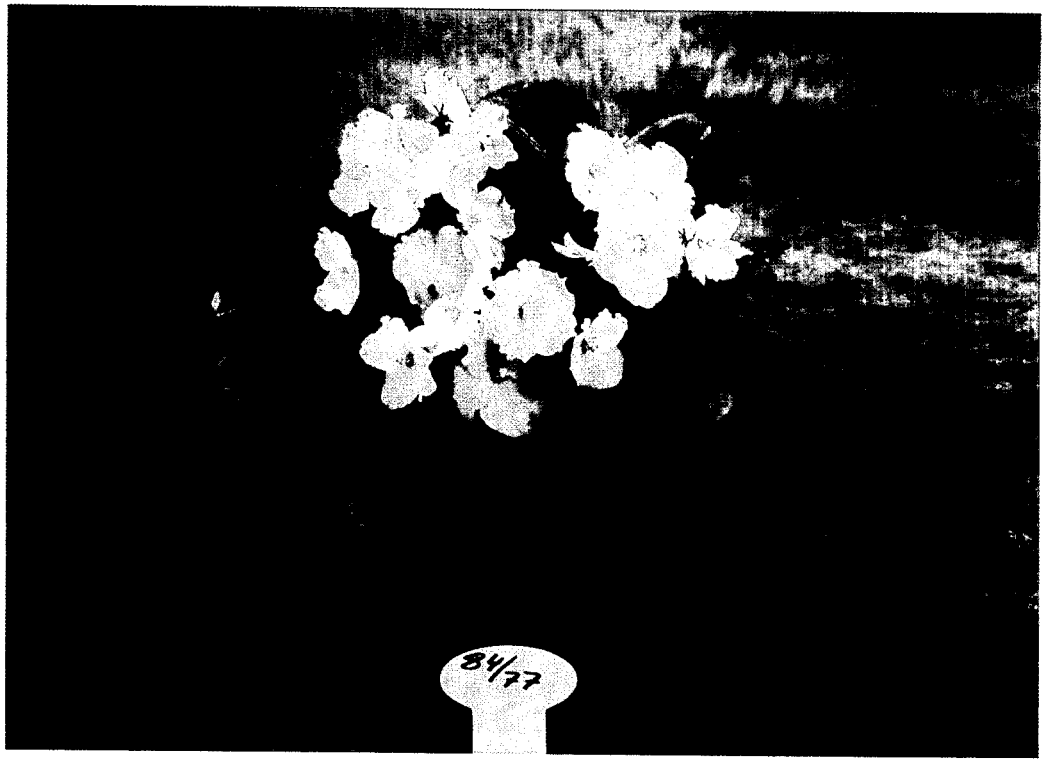
84/77